(12) United States Patent
Lung

(10) Patent No.: US 10,100,086 B2
(45) Date of Patent: Oct. 16, 2018

(54) PEPTIDE AND USES THEREOF

(71) Applicant: Tunghai University, Taichung (TW)

(72) Inventor: Feng-Di Lung, Taichung (TW)

(73) Assignee: TUNGHAI UNIVERSITY, Taichung (TW)

( * ) Notice: Subject to any disclaimer, the term of this patent is extended or adjusted under 35 U.S.C. 154(b) by 0 days.

(21) Appl. No.: 15/710,491

(22) Filed: Sep. 20, 2017

(65) Prior Publication Data

US 2018/0009846 A1    Jan. 11, 2018

Related U.S. Application Data

(62) Division of application No. 14/934,560, filed on Nov. 6, 2015, now Pat. No. 9,802,982.

(30) Foreign Application Priority Data

Nov. 10, 2014   (TW) .............................. 103138945 A
Oct. 22, 2015   (TW) .............................. 104134739 A

(51) Int. Cl.
*A61K 38/08* (2006.01)
*C07K 7/06* (2006.01)
*A61K 38/00* (2006.01)

(52) U.S. Cl.
CPC ................ *C07K 7/06* (2013.01); *A61K 38/00* (2013.01); *Y02A 50/473* (2018.01)

(58) Field of Classification Search
None
See application file for complete search history.

(56) References Cited

U.S. PATENT DOCUMENTS 9,802,982 B2 * 10/2017 Lung ...................... C07K 7/06

OTHER PUBLICATIONS

Lung FD, Discovery of potent antimicrobial peptide analogs of Ixosin-B, Bioorg Med Chem Lett. Jun. 15, 2012; 22 (12):4185-8.
Hsiao YC, Anticancer activities of an antimicrobial peptide derivative of Ixosin-B amide, Bioorg Med Chem Lett. Oct. 15, 2013; 23(20):5744-7.
Chatteriee J, N-methylation of peptides: a new perspective in medicinal chemistry Acc Chem Res. Oct. 2008; 41 (10)1331-42.

* cited by examiner

*Primary Examiner* — Satyanarayana R Gudibande
(74) *Attorney, Agent, or Firm* — Ming Chow; Sinorica, LLC

(57) ABSTRACT

This present invention provides a novel peptide for inhibiting growth of microorganisms, a pharmaceutical composition, an antimicrobial composition comprising such novel peptide, and a method for inhibiting growth of microorganisms. The novel peptide for inhibiting growth of microorganisms has amino acid sequence: $KX_1LRX_2X_3X_4RRWX_5$, wherein $X_1$, $X_2$, and $X_5$ are selected from the group of W and R, respectively; $X_3$ is selected from the group of V and P; and $X_4$ is selected from the group of R and methylated W. The method for inhibiting growth of microorganisms disclosed in this present invention comprises administering the novel peptide, the pharmaceutical composition, or the antimicrobial composition.

4 Claims, 2 Drawing Sheets

Specification includes a Sequence Listing.

PEPTIDE AND USES THEREOF

BACKGROUND OF THE INVENTION

1. Field of the Invention

This invention relates to an artificial synthesis protein, specially relates to a novel peptide and uses thereof.

2. Description of the Related Art

Many bacteria have drug resistance because of abuse of antibiotics in recent years. For example, about more than half of *Staphylococcus aureus* found in intravenous catheters are resistant to Penicillin. Drug resistant bacteria give anti-antibiotic genes to next generation through plasmid, which causes that drug resistant bacteria can't be eliminated effectively. This situation leads to a serious problem when treating related diseases caused by bacteria.

In order to avoid shortcomings of traditional antibiotics, many researches recently focus on developing the antimicrobial peptide to assist organism in resisting or eliminating foreign pathogens. To be more specifically, the antimicrobial peptide has the following advantages over traditional antibiotics. First, the antimicrobial peptide has broad and rapid antimicrobial activity and a smaller effective dosage which is unlikely to cause drug resistance of microbacteria. Second, the antimicrobial peptide can stimulate immune cell of a organism to increase immunity of the organism against diseases.

Hence, there are few antimicrobial peptides used for drug preparation. For example, Magainin (Pexiganan) is applied for treating diabetic foot ulcers. Indolicidin (MBI-549) is applied for treating acne. Although the antimicrobial peptide have plenty of types and good antimicrobial activity, however, when the conformation of a antimicrobial peptide is linear, the antimicrobial peptide may be hydrolyzed by enzymes and lose its activity in vivo. To make the antimicrobial peptide is less susceptible to enzyme hydrolysis in vivo, in further to increase stability of the antimicrobial peptide against enzymes. Recent development of the antimicrobial peptide mainly focus on cyclic peptides. However, although the antimicrobial activity of the antimicrobial peptide is maintained in vivo by changing the conformation, it still needs to improve the safety of the antimicrobial peptide for human body. For example, the antimicrobial peptide can effectively and safely apply on human body only when the side effect, such as hemolysis, is controlled.

Accordingly, it is the most important challenge for researchers to develop an antimicrobial peptide with good antimicrobial activity and high safety.

SUMMARY OF THE INVENTION

The major propose of this present invention is to provide a novel peptide which can resist bacteria effectively and avoid producing drug resistant pathogens.

Further another purpose of this present invention is to provide a novel peptide having low hemolysis which can reduce side effects and risks of organisms.

Further another purpose of this present invention is to provide a pharmaceutical composition which by administering an effective dosage of the peptide disclosed in this present invention to a subject to inhibit growth of microorganisms for treating diseases caused by microorganisms and with good safety to human.

Further another purpose of this present invention is to provide an antimicrobial composition which can effectively inhibit growth of microorganisms to prevent the harm caused by microorganisms to organisms.

In order to achieve these foresaid purposes, a preferable embodiment of this present invention discloses a novel peptide comprising the following amino acid sequence: $KX_1LRX_2X_3X_4RRWX_5$, wherein $X_1$, $X_2$, and $X_5$ are selected from the group consisting of W and R, respectively; $X_3$ is selected from the group consisting of V and P; and $X_4$ is selected from the group consisting of R and methylated W.

The novel peptide disclosed by this present invention has effect of inhibiting growth of microorganisms and low hemolysis. Hence, the novel peptide disclosed by this present invention can be administrated to a subject safely.

In another preferable embodiment of this present invention, the amino acid sequence of the novel peptide is SEQ ID NO. 1 in which has the seventh amino acid methylated.

In another preferable embodiment of this present invention, the amino acid sequence of the novel peptide is SEQ ID NO. 2.

In another preferable embodiment of this present invention, the amino acid sequence of the novel peptide is SEQ ID NO. 3.

In the embodiments of this present invention, the novel peptide can be produced by other methods known by person skilled in the art of this present invention and having general knowledge. For example, these methods comprise artificial synthetic technique, platform for recombinant protein expression, etc. Preferably, the novel antimicrobial peptide of present invention can be synthetized by solid phase peptide synthesis.

Another embodiment of this present invention discloses a pharmaceutical composition which comprises an effective dosage of the novel peptide disclosed in this present invention and at least a pharmaceutical acceptable carrier. By administering the pharmaceutical composition to a subject, growth of microorganisms in the subject can be inhibited and hence the disease caused by the microorganisms is cured. In addition, because of the low hemolysis of the novel peptide disclosed in this present invention, when administering to the subject, the novel pharmaceutical composition will not induce hemolysis. Therefore, it can prevent or reduce dramatically the side effects induced by traditional antimicrobial pharmaceutical composition.

Generally speaking, the microorganisms are pathogens comprising but not limited to *Escherichia coli*, *Staphylococcus aureus*, or *Pseudomonas aeruginosa*.

In one embodiment of this present invention, the antimicrobial composition at least comprises an effective dosage of any one of the antibacterial peptides mentioned above.

The antimicrobial composition can be produced as different forms depends on needs. The forms comprise but not limited to spray, liquid, solid, and jelly etc. In addition, the antimicrobial composition can be used externally, internally, and used as environmental product with different formulations.

By using the antimicrobial composition, growth of the microorganisms can be effectively controlled to prevent inflammation on a organism caused by microorganisms or to prevent destruction of environment or goods. The microorganisms are pathogens comprising but not limited to *Escherichia coli*, *Staphylococcus aureus*, or *Pseudomonas aeruginosa*.

DETAILED DESCRIPTION OF THE INVENTION

Figure 1:
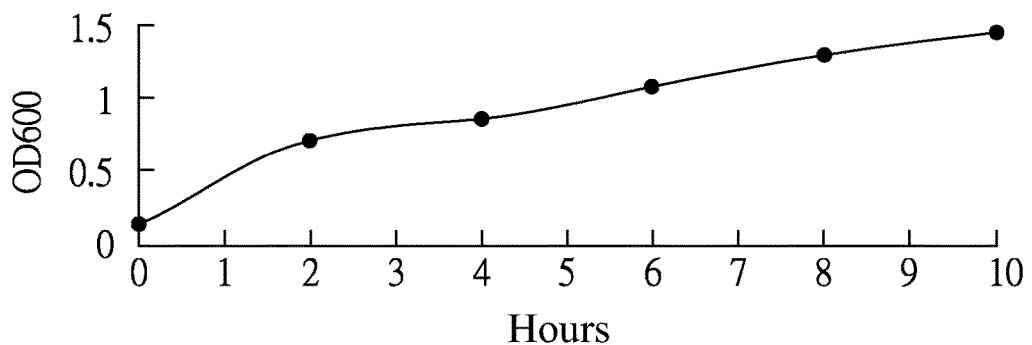
FIG. 1 is the growth curve of *Escherichia coli*.

The meaning of the technological and scientific terms disclosed in the specification and claims of this present invention is the same as the understanding from a person skilled in the art of this present invention and having general knowledge. The content of this present invention is the first priority of explanation if there are contraries.

The "artificial synthesis technique" is a common technique known by an ordinary person skilled in the art of this present invention. The artificial synthesis technique artificially chains amino acids in sequence to produce a polypeptide, wherein the artificial synthesis technique comprises chemical synthesis method and a peptide synthesizer. Usually the artificial synthesis technique has the following advantages: conveniently changing the primary structure of a polypeptide during the process of artificial synthesis, adding special amino acids, and modifying the end of polypeptide. Generally speaking, the artificial synthesis technique is classified as solid phase peptide synthesis and liquid phase peptide synthesis. The liquid phase peptide synthesis has to extract intermediate product after each time of amino acid chain reaction. As the intermediate product of each extraction is usually mixtures, chromatographic purification is needed to purify the mixtures. Hence, synthesis of the polypeptide by liquid phase peptide synthesis has to involve many complicated extractions and purifications to obtain high plurality product. The solid phase peptide synthesis performs amino acid chain reactions on solid polymeric particles (or polymeric supports) in solvent. During the process of solid phase peptide synthesis, first of the amino acid of a target polypeptide as the N-terminal end is covalently attached to a solid polymeric particle, then the following amino acids are linked to the first amino acid by specific covalent bonds, and finally the peptide is synthesized. Due to the fact that the polymeric particle is insoluble in the solvent, so the solid polymeric particles and the peptide attaching on the solid polymeric particles can be separated from the solvent and side products by washing and filtering at the end of synthesis. As purifications are not required, the solid phase peptide synthesis not only has higher yield but also significantly shorten reaction time and is superior in long chain polypeptide synthesis. Therefore, the solid phase peptide synthesis is commonly used in peptide synthesis.

The "platform of recombinant protein expression" means construction of a nucleic acid sequence which expresses a specific protein on an expression vector through biotechnology. The recombinant expression vector is then transformed into a host cell such as *Escherichia coli*, yeast bacteria, lactic acid bacteria, etc. to obtain the specific protein by expression the nucleic acid sequence in the host cell.

The "effective dosage" means the amount of compound or active ingredient to generate specific effect. It can be shown as the weight percentage in a composition. It can be understood by the person skilled in the art of this present invention and having general knowledge that the effective dosage will be different because of the administering pathway which is trying to induce specific effect. Generally speaking, the amount of the active ingredient or compound in the composition can take about 1% to about 100% of weight, the better one will be about 30% to about 100% of weight.

The "pharmaceutical composition" includes an effective dosage of compound or active ingredient which is necessary to produce specific effect, and at least a pharmaceutical acceptable carrier. It can be understood by the person skilled in the art of this present invention and having general knowledge that the type of composition can be different according to the administering pathway such as tablet, powder, injection, etc. The carrier also can be solid, semi-solid or liquid according to the type of the composition. For example, the carrier comprises but not limited to gelatin, emulsifiers, hydrocarbon mixtures, water, glycerin, physiological saline, buffered physiological saline, lanolin, paraffin wax, beeswax, dimethicone or ethanol.

The "pharmaceutical acceptable carrier" is compatible with the active ingredient of a pharmaceutical composition. Preferably, the pharmaceutical acceptable carrier can increase the stability of the pharmaceutical composition and with no harm to a subject. According to the type of the pharmaceutical composition, the pharmaceutical acceptable carrier comprises but not limited to corn starch, lactose, cellulose, magnesium stearate, colloidal silicon oxide, maltodextrin, water, etc.

The "a/an" or "the" in the specification and the claims of present invention means one and more than one unless otherwise stated.

Hereinafter, there are several examples for further illustrating the effect of this present invention. But these examples are only for explanation. Any words mentioned do not tend to limit the scope and meaning of the specification and claims of this present invention.

Example 1: Solid Phase Peptide Synthesis

In the example 1, the Fmoc solid phase peptide synthesis was used to synthesize the target peptide.

First, the amount of the amino acid, HOBT (Scientific), HBTU (Agene Max), DIEA (SIGMA), the resin support (PAL Rink resin, NOVA Biochem, San Diego, Calif., USA) needed during the synthesis were calculated. A filter and the resin support was sequentially placed into a PD-10 column (17-0435-01, Amersham Biosciences) and then 5 mL dichloromethane (DCM) was added into the PD-10 column to expand the resin supports. The liquid in the PD-10 column was then drawn out and waited 5 minutes for reaction. The above mentioned steps were repeated 2 times. 5 mL dimethylformamide (DMF) was then added into the PD-10 column to keep the resin support moisture. The remaining DCM was washed, waited 5 minutes for reaction, and the liquid in the PD-10 column was then removed.

Next, synthesis was proceeded. 5 mL, 20-30% (v/v) piperidine was added into the PD-10 column to remove the No.-Fmoc protection group of the resin support. After 15 minutes reaction, the liquid in the PD-10 column was removed. The amino acid with No.-Fmoc protection group, HOBT, HBTU, DIEA and 5 mL DMF were mixed for 1 minute to activate the C-terminal of the amino acid. The mixture was added into the PD-10 column to proceed amino acid coupling reaction for 2 hours to attach the amino acids and the Knorr resin. After that, the liquid in the PD-10 column was removed. 5 mL DMF was added into the PD-10 column to wash unreacted amino acids and reagent, and then removed the liquid in the PD-10 column. The above mentioned synthesis procedures were repeated to attach amino acids to the resin support in sequence.

During the process of synthesis, Ninhydrin test was used to test whether the coupling is successful. The procedures of Ninhydrin test lists as follows: 10 μL Ninhydrin test reagent was placed into a test tube and a few resin supports were placed into the test tube as well. The test tube was heated by an oil bath of 95° C. for 5 minutes. The coupling succeeded if these resin supports became transparent or yellow. After that, these resin supports attached next amino acid after DMF washing. The coupling failed if these resin supports became dark blue and one more repeated coupling was needed.

After the synthesis terminated, 5 mL, 20-30% (v/v) piperidine was added into the PD-10 column in sequence for 15 minutes to remove the No.-Fmoc protection group of the peptide and then to the side chain protection group of the peptide. The target peptide detached from the resin support via chemical cleavage. Crude product of the linear peptide was obtained after vacuum filtration of the target peptide and drying the filtrate.

Example 2: Synthesizing Methylated Peptide

First, peptide was synthesized by solid phase peptide synthesis and attached on resin support. Next, o-NBS-Cl (4 eq) and collidine (10 eq) were added into 2 mL N-Methyl-2-Pyrrolidone (NMP), which is the protection agent of N-terminal and catalyst reagent. After reacting for 15 minutes, the resin support was washed by NMP for 5 times to obtain amino acids with N-terminal having o-NBS protection group. After that, catalyst DBU (3 eq) was mixed with 1 mL NMP for pre-activation. Then, dimethyl sulfate (10 eq) and 1 mL NMP, which is a methylation reagent, were added to proceed methylation reaction with the amino acid with N-terminal having o-NBS protection group to obtain Na-Methyl-Na-o-NBS-peptides. Then, a deprotection reagent was prepared by mixing DBU (5 eq), 2-mercaptoethanol (10 eq), and 2 mL N-Methylpyrrolidine. The deprotection reagent was added into the reaction column for 1 hour and repeated 2 times to remove o-NBS protection group to obtain N-methylated peptides. Then, amino acid coupling reaction was proceeded by solving the next amino acid (3 eq), HATU (3 eq), HOAt (3 eq) and DIEA (6 eq) in 4 mL NMP as a coupling reagent. Repeated the above mentioned steps until all the amino acid was attached on the resin support. Finally, the side chain protection group was removed and cleavage of the peptide from the resin support by TFA as a cleavage reagent for hours shaking. Crude product of the methylated peptide was obtained by filtering and purifying the filtration.

Example 3: Purifying Peptide

A semi-preparative column on a reverse phase-high performance liquid chromatography (RP-HPLC) was used to confirm the plurality and retention time of crude product of the peptide and proceeding purification thereof. Wherein the column was 5 μm $C_{18}$ column and the flow rate of the mobile phase was 4 mL per minute. The composition of the mobile phase was solvent A for 4 L distilled deionized water (0.22 μm filter membrane) and 2 mL, 0.05% trifluoroacetate, and solvent B for 4 L acetonitrile and 2 ml, 0.05% trifluoroacetate. The detection wavelength was 225 nm. And finally, the purified product was frozen dried to obtain peptide powder.

Example 4: Identifying Molecular Weight of the Peptide

The molecular weight of the synthesized peptide was identified by matrix-assisted laser desorption/ionization time-of-flight mass spectrometry (MALDI-TOF).

The sample and the matrix solution (CHCA) having absorption in laser energy were mixed evenly with a mixing ratio of 1:1. 1 μL of the foresaid mixture was placed on the sample tray and waited until the volatile solvent evaporated. The matrix and the sample became a solid cocrystal on the sample tray and the cocrystal was then send into the ion source of MALDI-TOF to receive pulsed laser irradiation for desorption in vacuum. After that, the m/z ratio was measured by the mass analyzer to evaluate the molecular weight.

Example 5: Preparing Peptide

Prepared peptides listed in Table 1 by the methods described in example 1 to 4, wherein "Me" means the amino acid after "Me" has been methylated.

TABLE 1

Synthesized peptides and amino acid sequence thereof

| peptide | SEQ ID No of amino acid sequence | amino acid sequence |
|---|---|---|
| Peptide 1 | SEQ ID No. 1, wherein the 7$^{th}$ amino acid is methylated | KWLRRVMeWRWWR |
| Peptide 2 | SEQ ID No. 2 | KWLRRPWRRWR |
| Peptide 3 | SEQ ID No. 3 | KWLRWVRRRWW |
| Peptide 4 | SEQ ID No. 4, wherein the 7$^{th}$ amino acid is methylated | KRLRRVMeWRWWR |
| Peptide 5 | SEQ ID No. 1, wherein the 5$^{th}$ amino acid is methylated | KWLRMeRVWRWWR |
| Peptide 6 | SEQ ID No. 1 | KWLRRVWRWWR |

Example 6: Microbiological Culture

Three bacteria strains, *Escherichia coil* (ATCC 25922), *Staphylococcus aureus* (ATCC25923), and *Pseudomon asaeruginosa* (ATCC27853) were brought from the Food Industry Research and Development Institute, Hsinchu, Taiwan.

Each of the strain (0.1-0.2 mL) was inoculated on an agar gel medium (Merck, Whitehouse, Station, N.J., USA) and isolated into single colony by streak plate method. Each of the strain was spread evenly by a sterile L-shaped glass rod and incubated overnight. After that, the single colony on each agar gel medium was transferred to liquid LB medium (Merck, Whitehouse, Station, N.J., USA) and incubated at 37° C. in an incubator.

After overnight incubation, the broth containing each of the strains was diluted with sterile water in different ratio. The dilution ratio of the broth and sterile water are 1:2, 1:4, 1:8, 1:16, 1:32, and 1:64. Optical density of each diluted broth was measured at 595 nm ($OD_{595}$) by a UV spectrometer to evaluate the number of bacteria in the broth and to plot the standard growth curve.

Figure 2:
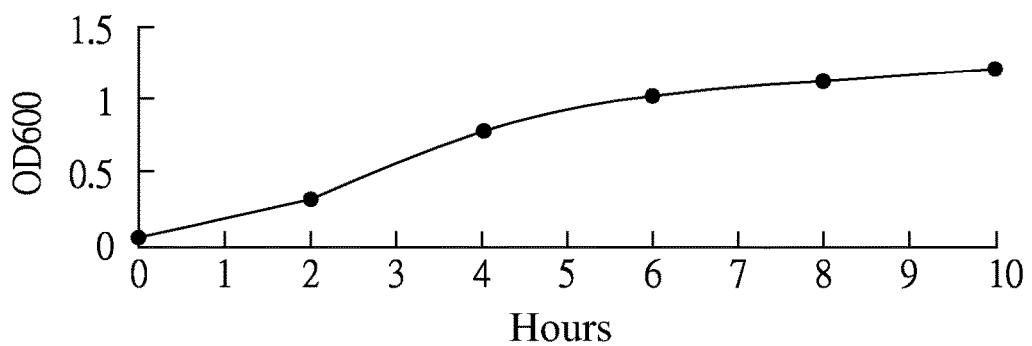
FIG. 2 is the growth curve of *Staphylococcus aureus*.
Figure 3:
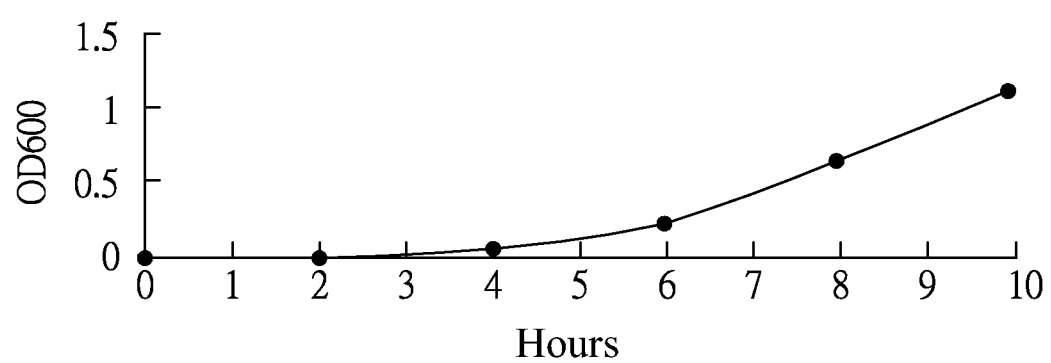
FIG. 3 is the growth curve of *Pseudomonas aeruginosa*.

The growth curve of Escherichia colt, Staphylococcus aureus, and Pseudomonas aeruginosa was obtained respectively by the above mentioned steps and shown in FIG. 1 to FIG. 3.

Example 7: Antimicrobial Test

Each bacteria strain from example 6 was incubated to its mid-log phase at 37° C. in 2 mL Lysogeny broth (LB) in an incubator, wherein the mid-log phase of Escherichia coil is 4 hours, the mid-log phase of Staphylococcus aureus is 6 hours, and the mid-log phase of Pseudomonas aeruginosa is 8 hours. According to 0.5 McFarland Standard, the number of bacteria in a broth is $1 \times 10^8$ CFU/mL when the $OD_{595}$ is 0.08-0.09. Hence, each of the bacterial broth was diluted with sterile water to have the same $OD_{595}$ of 0.5 McFarland Standard. And then, the number of bacteria in each broth was diluted from $1 \times 10^8$ CFU/mL to $1 \times 10^5$ CFU/mL. Finally, each broth has bacterial number of $5 \times 10^5$ CFU/mL in Mueller Hinton broth (MHB).

199 μL of each of the foresaid diluted broth was respectively placed into a 96 well plate, and 1 μL of each peptide from example 5 was added into each well to incubate at 37° C. in an incubator for 16 hours. The $OD_{595}$ of the coculture of each broth and each peptide was measured by a microplate spectrophotometer. In addition, the bacterial broth without the peptide served as positive control (PC), and the free broth MHB culture medium served as negative control (NC). The minimum inhibitory concentration (MIC90) of each peptide against each bacteria was measured according to the following equation, wherein A is the absorbance. The MIC90 results are listed in Table 2.

$$MIC90 \leq [(A_{peptide} - A_{NC})/(A_{PC} - A_{NC})]$$

In addition, to measure the minimum bactericidal concentration (MBC), 1 μL of each broth cocultured with the peptide was sprayed on a flat plate medium at 37° C. in an incubator for 24 hours. If the incubation result has no bacteria, the concentration of the reagent is MBC. The MBC results are listed in Table 3.

TABLE 2

Minimum inhibitory concentration (MIC90) of each peptide against bacteria

| | Minimum inhibitory concentration (MIC90) (μM) | | |
|---|---|---|---|
| | Escherichia coli | Staphylococcus aureus | Pseudomonas aeruginosa |
| peptide 1 | 5 | 5 | 10 |
| peptide 2 | 2.5 | 2.5 | 5 |
| peptide 3 | 2.5 | 2.5 | 5 |
| peptide 4 | 20 | 10 | 20 |
| peptide 6 | 5 | 5 | 5 |

TABLE 3

Minimum bactericidal concentration (MBC) of each peptide against bacteria

| | Minimum bactericidal concentration (MBC99.9) (μM) | | |
|---|---|---|---|
| | Escherichia coli | Staphylococcus aureus | Pseudomonas aeruginosa |
| peptide 1 | 20 | 40 | 10 |
| peptide 2 | 10 | 5 | 20 |
| peptide 3 | 10 | 5 | 20 |
| peptide 4 | 20 | 10 | 20 |
| peptide 6 | 5 | 10 | 5 |

From the results of Table 2 and Table 3, it can be understood that SEQ ID No. 1 which the $7^{th}$ amino acid is methylated, SEQ ID No. 2 and 3 have effect of inhibiting growth of microorganisms.

Example 8: Hemolysis Assay 1-3 mL human blood was centrifuged at 3000 rpm, 4° C. for 10 minutes. The supernatant was discarded. The remaining was washed with cold phosphate buffer saline (PBS) and centrifuged at 3000 rpm, 4° C. for 1 minute. The supernatant was discarded. The remaining red blood cells were washed and diluted as 2% red blood cell solution with cold PBS.

A mixture of 100 μL red blood cell solution and 100 μL PBS was served as a negative control. A mixture of 100 μL red blood cells solution and 100 μL 0.2% Triton X-100 was served as a positive control. The solution of peptide 1, peptide 2, peptide 3, peptide 5, and peptide 6 were respectively mixed with red blood cell solution with the same volume and incubated at 37° C. for 1 hour. After incubation, the mixture was centrifuged at 3000 rpm, 4° C. for 10 minutes. Each of the supernatant was collected to measure the absorbance at wavelength of 405 nm by an ELISA plate reader. The hemolysis of each peptide was calculated according to the following equation, wherein Abs represents the absorbance. The hemolysis results are listed in Table 4.

$$[(Abs_{peptide} - Abs_{PBS})/(Abs_{Triton\ X-100} - Abs_{PBS})] \times 100$$

TABLE 3

Hemolysis of each peptide

| | Hemolysis (%) |
|---|---|
| peptide 1 | 20.1 |
| peptide 2 | 3.4 |
| peptide 3 | 3.4 |
| peptide 5 | 44.9 |
| peptide 6 | 70.7 |
| Negative control | 0 |
| Positive control | 100 |

From the results of Table 4, it can be understood that hemolysis of the peptide 1-3 were obviously lower than that of the peptide 5 and 6, wherein the peptide 2 and 3 were the lowest. As known by the person skilled in the art of this present invention and having general knowledge, high hemolysis breakdowns red blood cells of a subject and induces side effects such as anemia, pain, etc. It can even induce much more serious side effects which endanger life. In other words, because of lower hemolysis, administering the peptide 1-3 to a subject can lower risk to induce hemolysis, which means to induce minor side effects of the subject.

In addition, although there are methylation in amino acid sequence of the peptide 1 and 5, but according to different methylation position, the hemolysis of the peptide 1 is significantly lower than the peptide 5. It can be understood that not every methylated peptide can significantly avoid hemolysis.

Furthermore, it can be understood from the results of Table 2 to 4 that even the peptide 6 has antimicrobial activity, but the hemolysis of peptide is higher than the peptide 1, peptide 2, and peptide 3. A subject will face an elevated risk of hemolysis if the peptide 6 is administered. Therefore, the peptide having high hemolysis cannot become or apply as a pharmaceutical composition or an antimicrobial composition.

From the results of foresaid examples, it can be understood that the novel peptide disclosed in present invention has great antimicrobial activity and low hemolysis, and thus to become effective ingredient of a pharmaceutical composition or an antimicrobial composition which can be administered to a subject safely.

From the results of foresaid examples, it can be understood that the novel peptide disclosed in present invention has following advantages:

First, the novel peptide disclosed in this present invention has antimicrobial activity to inhibit variable pathogens. Hence, the peptide can become the effective ingredient of a pharmaceutical composition or an antimicrobial composition which having antimicrobial activity in daily life or clinically.

Second, the novel peptide disclosed in this present invention can reduce much more side effects of a subject and have higher safety while having antimicrobial activity.

Third, the novel peptide disclosed in this present invention can prevent to induce drug resistance of pathogens, which much more improve the lacks of traditional antibiotics.

The above-mentioned detailed description and specific examples are given for illustration of this present invention only. Any easy changes or modifications base on examples in the description by the person skilled in the art of this present invention will be included within the scope of following claims.

What is claimed is:

1. A synthetic peptide comprising the amino acid sequence: SEQ ID NO.2.

2. The peptide of claim 1, wherein the peptide is produced by solid phase peptide synthesis.

3. A pharmaceutical composition comprising an effective dosage of the peptide of claim 1 and a pharmaceutical acceptable carrier.

4. An antimicrobial composition comprising the peptide of claim 1.

* * * * *

SEQUENCE LISTING

```
<160> NUMBER OF SEQ ID NOS: 4

<210> SEQ ID NO 1
<211> LENGTH: 11
<212> TYPE: PRT
<213> ORGANISM: Artificial Sequence
<220> FEATURE:
<223> OTHER INFORMATION: artificial synthesis

<400> SEQUENCE: 1

Lys Trp Leu Arg Arg Val Trp Arg Trp Trp Arg
1               5                   10

<210> SEQ ID NO 2
<211> LENGTH: 11
<212> TYPE: PRT
<213> ORGANISM: Artificial Sequence
<220> FEATURE:
<223> OTHER INFORMATION: artificial synthesis

<400> SEQUENCE: 2

Lys Trp Leu Arg Arg Pro Trp Arg Arg Trp Arg
1               5                   10

<210> SEQ ID NO 3
<211> LENGTH: 11
<212> TYPE: PRT
<213> ORGANISM: Artificial Sequence
<220> FEATURE:
<223> OTHER INFORMATION: artificial synthesis

<400> SEQUENCE: 3

Lys Trp Leu Arg Trp Val Arg Arg Arg Trp Trp
1               5                   10

<210> SEQ ID NO 4
<211> LENGTH: 11
<212> TYPE: PRT
<213> ORGANISM: Artificial Sequence
<220> FEATURE:
<223> OTHER INFORMATION: artificial synthesis
```

```
<400> SEQUENCE: 4

Lys Arg Leu Arg Arg Val Trp Arg Trp Trp Arg
1               5                   10
```